United States Patent [19]
Speirs

[11] Patent Number: 5,834,021
[45] Date of Patent: Nov. 10, 1998

[54] PREDNISOLONE METASULPHOBENZOATE PREPARATION FOR THE TREATMENT OF INFLAMMATORY BOWEL DISEASE

[76] Inventor: Christopher J. Speirs, 82 Lower Road, Fetcham, Leatherhead, Surrey KT22 9NG, United Kingdom

[21] Appl. No.: 776,701

[22] PCT Filed: Aug. 11, 1995

[86] PCT No.: PCT/GB95/01900

§ 371 Date: Feb. 11, 1997

§ 102(e) Date: Feb. 11, 1997

[87] PCT Pub. No.: WO96/04918

PCT Pub. Date: Feb. 22, 1996

[30] Foreign Application Priority Data

Aug. 12, 1994 [GB] United Kingdom .................. 9416310

[51] Int. Cl.⁶ ............................. A61K 9/16; A61K 9/26; A61K 9/56; A61K 9/58
[52] U.S. Cl. .................... 424/490; 424/488; 424/499; 424/494; 424/495; 424/497; 424/470; 424/458; 424/461; 424/462
[58] Field of Search .................................. 424/484, 488, 424/425, 499, 494–95, 497, 469–70, 480–81, 458, 461–62, 490; 514/781, 925

[56] References Cited

U.S. PATENT DOCUMENTS

| | | |
|---|---|---|
| 4,285,987 | 8/1981 | Ayer et al. . |
| 5,004,613 | 4/1991 | Radebaugh et al. . |
| 5,007,790 | 4/1991 | Shell ........................................ 424/451 |
| 5,049,394 | 9/1991 | Howard et al. . |
| 5,178,866 | 1/1993 | Wright et al. ........................... 424/473 |
| 5,316,774 | 5/1994 | Gury et al. . |
| 5,401,512 | 3/1995 | Rhodes et al. . |

FOREIGN PATENT DOCUMENTS

| | | |
|---|---|---|
| 9011757 | 10/1990 | WIPO . |
| 9114426 | 10/1991 | WIPO . |

*Primary Examiner*—Edward J. Webman

[57] ABSTRACT

The dissolution at pH 6.5 of prednisolone metasulphobenzoate or a pharmacologically acceptable salt thereof from a non-disintegratable solid enteric composition comprising the prednisolone metasulphobenzoate in an excipient matrix is increased by the presence in the matrix of a rheological modifying agent, especially croscarmellose, in an amount of at least 5 percent by weight of the composition but insufficient to cause disintegration. Preferably the composition is in the form of pellets coated with an enteric coating which is substantially insoluble below pH 7 and contained in a capsule or tablet coated with an enteric coating which is soluble at a pH in the range pH 5.5 to pH 7. The coated capsules and tablets are for use in the treatment of inflammatory bowel disease, especially ulcerative colitis and Crohn's disease.

14 Claims, 9 Drawing Sheets

PREDNISOLONE METASULPHOBENZOATE PREPARATION FOR THE TREATMENT OF INFLAMMATORY BOWEL DISEASE

The present invention relates to the use of prednisolone metasulphobenzoate (11,17-dihydroxy-21-[(3-sulphobenzoyl) oxy] pregna-1,4-diene-3 20-dione) and pharmacologically acceptable salts thereof, especially the sodium salt, in the treatment of inflammatory bowel disease. In particular, it provides a solid enteric pharmaceutical composition having relatively rapid dissolution at pH 6.5 of the prednisolone metasulphobenzoate from an excipient matrix and dosage forms containing pellets (or granules) of the composition unless it is clear from the context that the free ester is intended, the terms "Prednisolone metasulphobenzoate" and "PRED-MSB" are used herein to include pharmacologically acceptable salts of prednisolone metasulphobenzoate as well as the free ester.

Steroids are widely used to treat severe cases of inflammation of the large bowel, especially ulcerative colitis and Crohn's disease. Usually, they are administered orally or parenterally to provide a systemic effect or rectally by enema to provide a topical effect. Relatively high doses of steroids are required to treat severe cases of inflammatory bowel disease. However, systemic absorption produces serious side effects and, although absorption is lower with rectal administration, the use of enemas is inconvenient.

The most commonly used steroid in the oral treatment of inflammatory bowel disease is prednisolone (17,21-dihydroxypregna-1,4-diene-3, 11,20-trione) in the form of the free alcohol or an ester thereof, usually the acetate. Daily doses of 15 to 60 mg (calculated as the free alcohol) are required to treat severe cases of inflammatory bowel disease but absorption at these doses is harmful. Accordingly, present treatment with prednisolone is limited in both dosage and duration of therapy.

FR-A-5083M discloses compositions comprising a corticosteroid, enzyme, salicylate and a vitamin. Exemplified corticosteroids include PRED-MSB but no excipients are specified and there is no reference to the treatment of inflammatory bowel disease.

FR-A-8106M discloses combinations of corticosteroids with cobalamines. The exemplified corticosteroids include PRED-MSB but no excipients are specified and there is no reference to the treatment of inflammatory bowel disease.

U.S. Pat. No. 3,424,842 discloses a process for manufacturing tablets directly from a dry powder containing 1 to 10 wt % of a powdery polyethylene glycol, gelatin or non-starch polysaccharide. Prednisolone is amongst a lengthy list of therapeutically active compounds which can be present in the tablets but there is no mention of PRED-MSB or of the treatment of inflammatory bowel disease.

GB-A-1578850 discloses solid pharmaceutical formulations for oral administration comprising 5 to 80 wt % steroid, 1 to 8 wt % sodium starch glycolate and the remainder conventional oral excipients. The only exemplified formulations are blends in gelatin capsules. It is reported that the presence of the sodium starch glycolate enhances disintegration of the tablets in 0.1N HCl. Reference is made to prednisolone but there is no reference to PRED-MSB or of the treatment of inflammatory bowel disease.

WO 87/05804 discloses the use of super-disintegrants in amounts of greater than 10% to enhance the disintegration of compressed tablets or capsules and has particular, but not exclusive, application to tablets containing glucocorticoid steroids. "Super-disintegrants" are defined to be those disintegrants which can be used in a fractional amount of normal disintegrants, such as corn starch, to obtain the same effect. Specified super-disintegrants include modified starches (especially sodium starch glycolate), croscarmellose sodium, and crospovidone. The super-disintegrants can be used in compositions containing microcrystalline cellulose and/or lactose as excipients. Exemplified steroids include methyl-prednisolone and prednisone but there is no reference to prednisolone or PRED-MSB. Further, there is no reference to the treatment of inflammatory bowel disease.

It is stated in WO 87/05804 that rapid dissolution of a pharmaceutical agent from a tablet or capsule requires rapid disintegration of the tablet or capsule and that it was surprising that large amounts of super-disintegrants, which are reportedly normally used at concentrations below 8%, would provide rapid disintegration.

PRED-MSB is known to be more poorly absorbed from the colon than prednisolone or prednisolone acetate. Accordingly, it has been proposed in, for example, Ford et al (Aliment. Pharmacol. Therap. (1992) 6, 31–40) that ulcerative colitis should be treated with an oral dosage form of PRED-MSB coated with Eudragit™ S (available from R öhm Pharma GmbH, Darmstadt, Germany). Eudragit™ S is an anionic copolymer of methacrylic acid and methacrylic acid methyl ester in which the ratio of free carboxyl groups to ester groups is approximately 1:2 and has a mean molecular weight of 135,000. Use of such a coating to target a topically active substance to the colon had previously been disclosed in EP-A-0097651 and a corresponding Eudragit™ S-coated 5-aminosalicylic acid product (ASACOL™) intended for the topical treatment of ulcerative colitis and Crohn's disease has been available since 1982.

BRIEF DESCRIPTION OF THE DRAWINGS

In the accompanying drawings.

μm) containing 5% PRED-MSB; 40 wt % microcrystalline cellulose (Avicel™ PH 101), 45 wt % lactose and 10 wt % croscarmellose sodium (Ac-Di-Sol™) at pH 6.4 (◇).

Ford et al supra used tablets containing only 7.8 mg PRED-MSB (equivalent to 5 mg prednisolone) and hence it was necessary to administer several (8 to 12) tablets in order to obtain an effective dose. Accordingly, the present Inventors decided to increase the unit dose to 31.4 mg PRED-MSB (equivalent to 20 mg prednisolone). In order to avoid bolus formation and provide improved PRED-MSB distribution, they decided to use an oral dosage form in which pellets of PRED-MSB are coated with Eudragit™ S; a plurality of the coated pellets encapsulated in a capsule or compressed into a tablet; and the capsule or tablet coated with Eudragit™ L (available from Röhm Pharma GmbH, Darmstadt, Germany). Eudragit™ L differs from Eudragit™ S in that the ratio of free carboxylic groups to ester groups is approximately 1:1. Both Eudragit™ L and Eudragit™ S are insoluble in gastric juice (about pH 6) but only Eudragit L is readily soluble in intestinal juice below about pH 7. Dosage forms of this type for use in selectively administering a drug, such as a steroid or, especially, 5-aminosalicylic acid, to the intestine are disclosed in WO-A-9214452.

Figure 1:
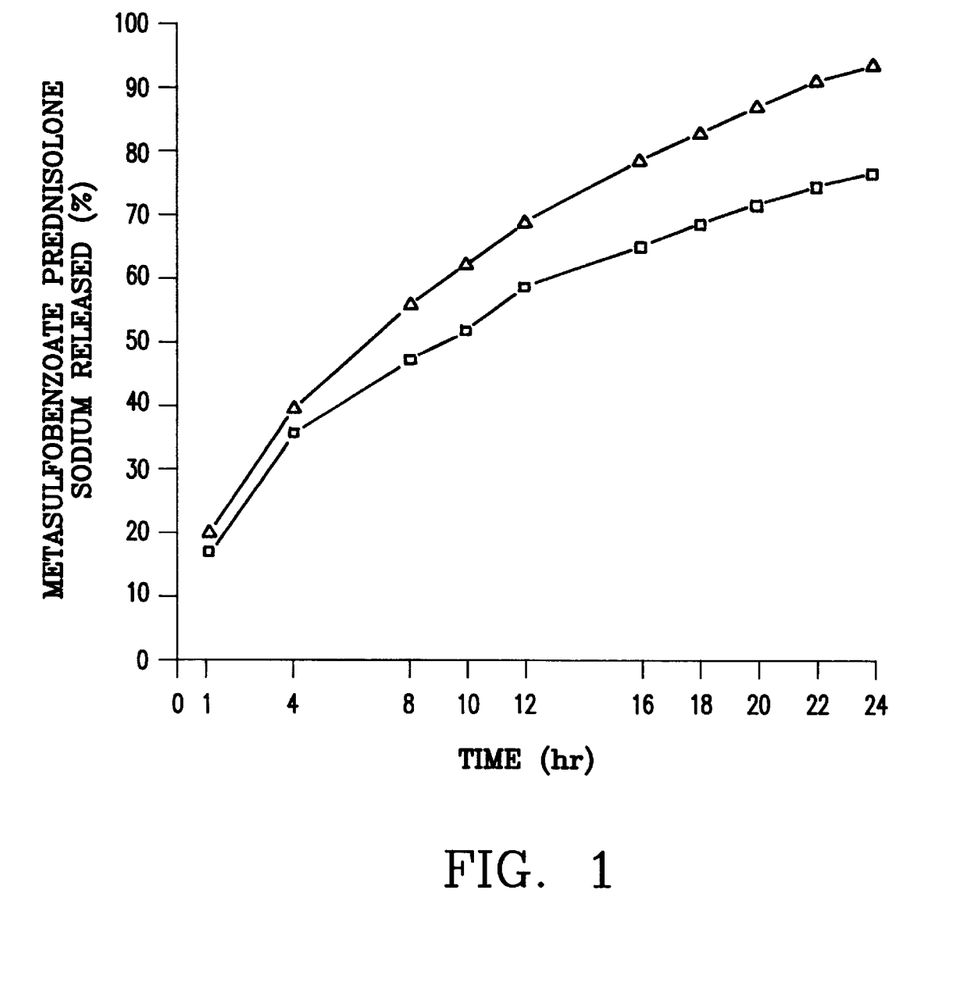
FIG. 1 shows the dissolution of 100 mg of pellets (700–1700 μm) containing 10 wt % PRED-MSB, 30 wt % microcrystalline cellulose (Avicel™ PH 101) and 60 wt % lactose at pH 6.4 (□) and pH 7.2 (Δ)
Figure 2:
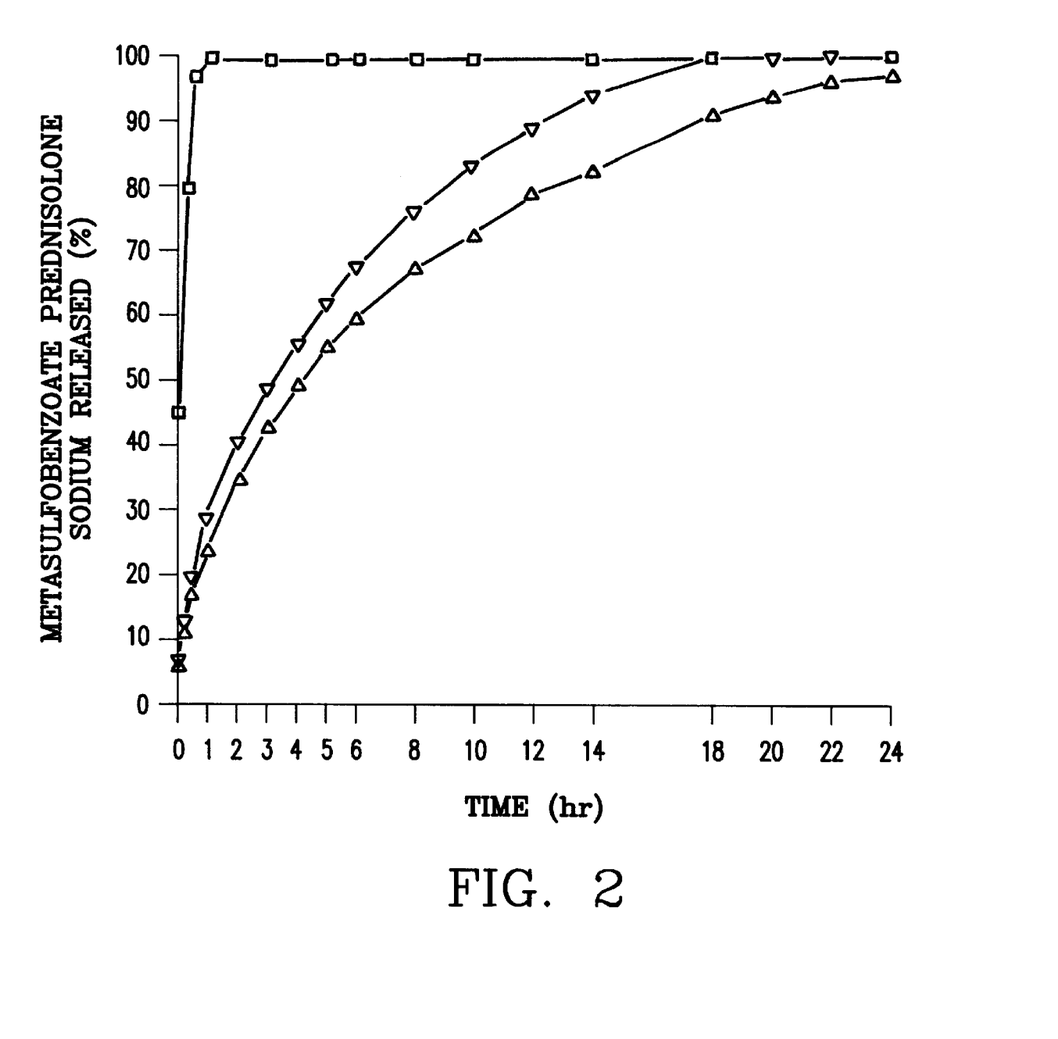
FIG. 2 shows the dissolution of 200 mg of pellets (700–1700 μm) containing 5 wt % PRED-MSB, 30 wt % microcrystalline cellulose (Avicel™ PH 101) and 65 wt % lactose at pH 1.2 (□) pH 6.4 (Δ) and pH 7.2 (∇)
Figure 3:
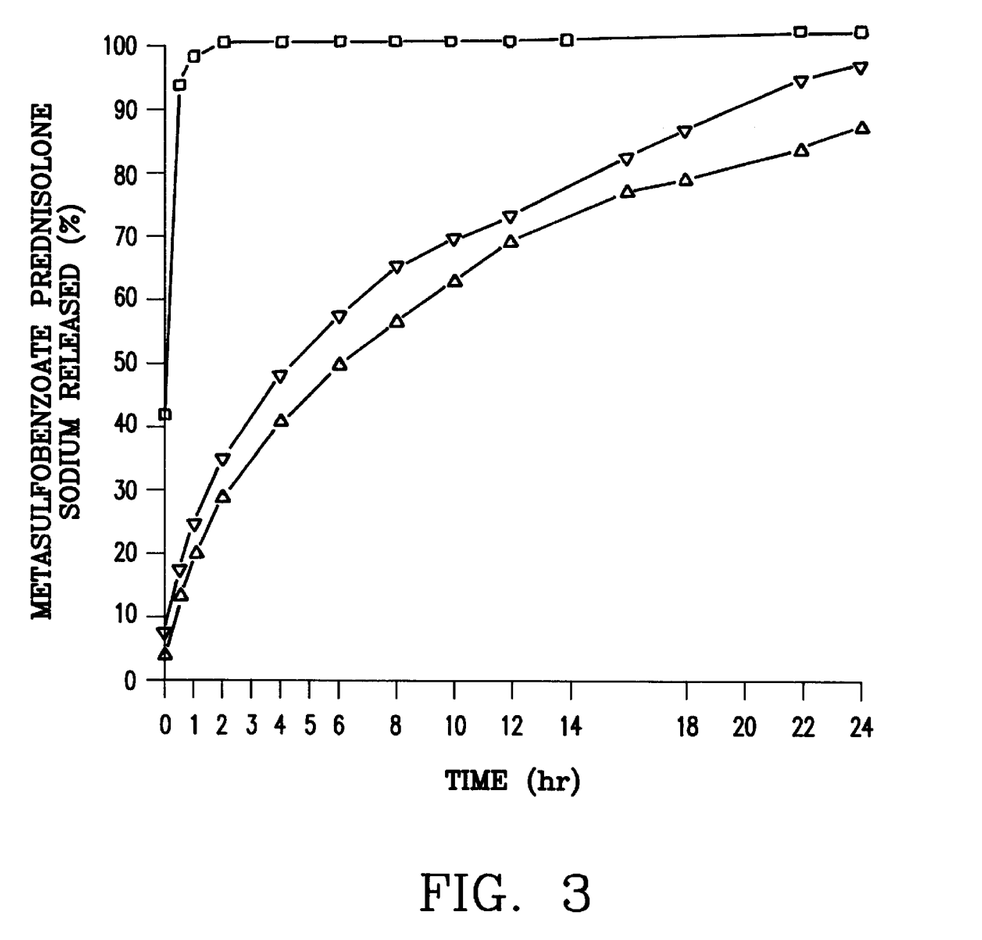
FIG. 3 shows the dissolution of 200 mg of pellets (700–1700 μm) containing 5 wt % PRED-MSB, 40 wt % microcrystalline cellulose (Avicel™ PH 101) and 55 wt % lactose at pH1.2 (□) pH 6.4 (Δ) and pH 7.2 (∇)

The pellets (700–1700 μm) were prepared from 5 wt % PRED-MSB with 30 wt % microcrystalline cellulose (Avicel™ PH 101) and 65% lactose. However, dissolution testing of the (uncoated) pellets revealed an unexpected dependence on pH in that PRED-MSB was substantially entirely released within 2 hours at pH 1.2 but at took more than 24 hours to substantially complete release the PRED-MSB at pH 6.4 or 7.2 (see FIG. 2). Moreover, the rate of dissolution at pH 6.4 or 7.2 decreased when the PRED-MSB concentration was increased from 5 wt % to 10 wt % with a corresponding decrease in lactose content from 65 wt % to 60 wt % (see FIG. 1). The rate of dissolution at pH 6.4 or 7.2 also decreased when the PRED-MSB concentration was maintained at 5 wt % to 10 wt % but the microcrystalline cellulose (Avicel™ PH 101) concentration increased to 40 wt % with a corresponding decrease in lactose content from 65 wt % to 55 wt % (see FIG. 3). Whilst not wishing to be bound by any theoretical considerations, it is now believed that the PRED-MSB forms a water-repellant matrix at higher pH.

Figure 4:
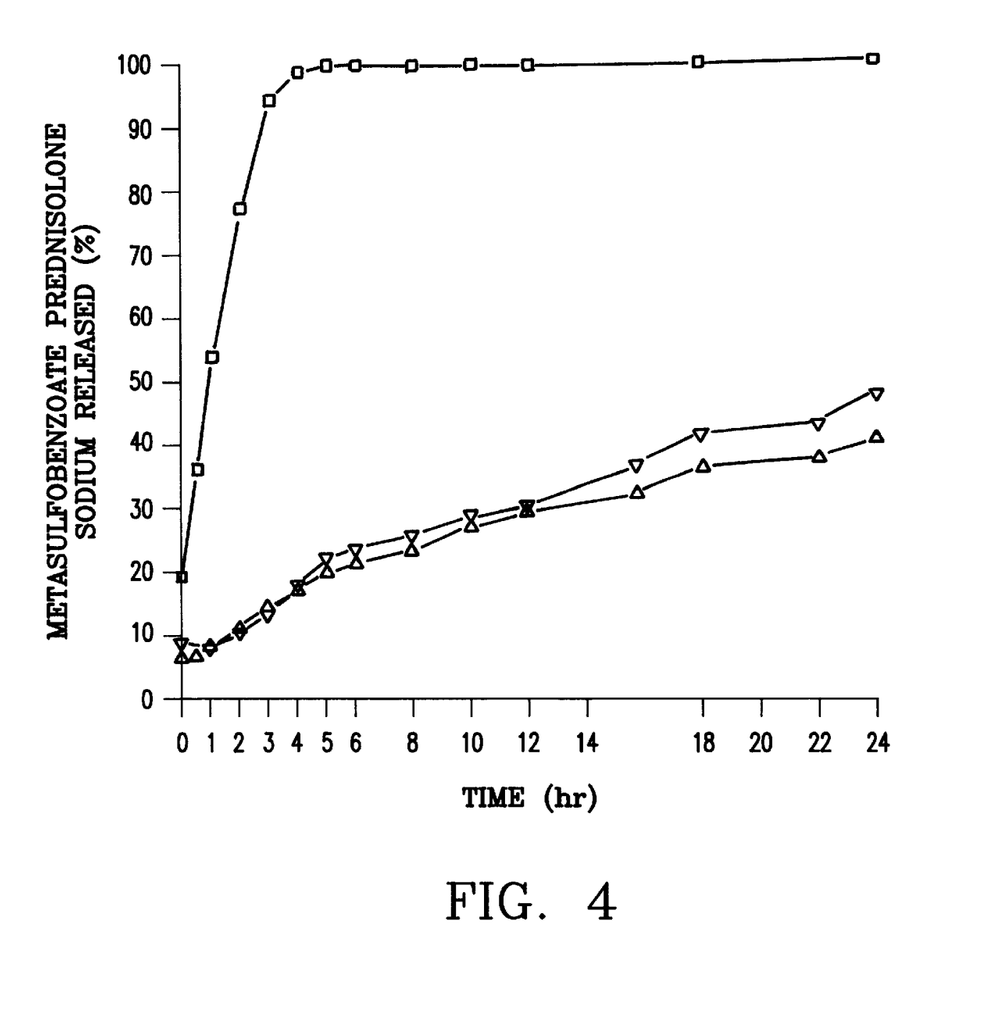
FIG. 4 shows the dissolution of 100 mg of pellets (700–1700 μm) containing 10 wt % PRED-MSB, 70 wt % microcrystalline cellulose (Avicel™ PH 101) and 20 wt % barium sulphate at pH 1.2 (□), pH 6.4 (Δ) and pH 7.2 (∇)
Figure 5:
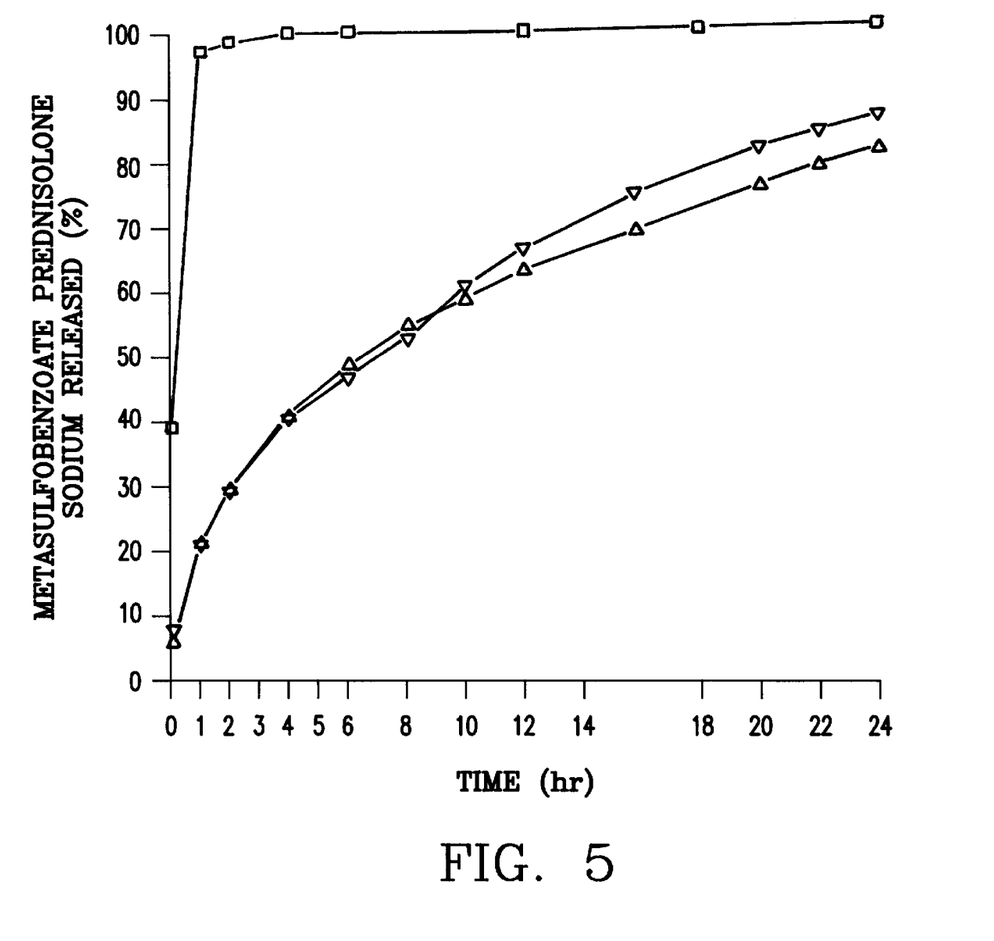
FIG. 5 shows the dissolution of 200 mg of pellets (700–1700 μm) containing 5 wt % PRED-MSB, 50 wt % microcrystalline cellulose (Avicel™ PH 101) and 45 wt % lactose at pH 6.4 with the addition of 0.1 wt % (Δ) or 1 wt % (∇) sodium lauryl sulphate and at pH 1.2 (□) in the absence of sodium lauryl sulphate.

Attempts were mace to improve the rate of dissolution and disintegration at higher pH by conventional practices such as altering the relative amounts of lactose and microcrystalline cellulose and/or adding barium sulphate or sodium lauryl sulphate (see FIGS. 4 & 5). However, such additions had little or no effect and throughout the experiments, the lack of disintegration was a feature.

Croscarmellose is a Cross-linked polymer of carboxymethylcellulose (carmellose) and is known for use in amounts of up to 2 wt % as a tablet disintegrant. Accordingly, it was expected that the addition of croscarmellose to the pellets would produce disintegration and thereby assist dissolution. However, at conventional levels croscarmellose had no effect on disintegration and prolonged dissolution. Higher concentrations of croscarmellose failed to produce disintegration but surprisingly the rate of dissolution at pH 6.4 or 7.2 increased with croscarmellose concentration (see FIGS 6, 7 & 8). At 20% croscarmellose consent, the pellets had similar dissolution profiles at pH 1.2 and pH 6.4 (see FIG. 9).

It is believed that other theological modifying, or viscosity increasing, super-disintegrants such as carmellose, crospovidone, sodium starch glycolates (ie sodium carboxymethyl starch), and starches (including processed starches) will show the same effect on the dissolution profile of the pellets as croscarmellose.

According to a first aspect of the present invention, there is provided a non-disintegratable solid enteric composition comprising prednisolone metasulphobenzoate or a pharmacologically acceptable salt thereof in an excipient matrix characterised in that the rate of dissolution of the prednisolone metasulphobenzoate at pH 6.5 is increased (compared with an otherwise identical composition) by the presence in the matrix of a rheological modifying super-disintegrant in an amount of at least 5 percent by weight of the composition but insufficient to cause disintegration thereof. By "non-disintegratable", we mean that the composition does not disintegrate sufficiently quickly at pH 6.4 to promote dissolution of the PRED-MSB content thereof.

In a second aspect, the invention provides the use of a rheological modifying super-disintegrant in an amount of at least 5 percent by weight of the composition, but insufficient to cause disintegration thereof, to increase the rate of dissolution at pH 6.5 of prednisolone metasulphobenzoate or a pharmacologically acceptable salt thereof from a non-disintegratable solid enteric composition comprising the prednisolone metasulphobenzoate in an excipient matrix.

In a third aspect, the invention provides an enterically administrable pharmaceutical dosage form for selectively administering prednisolone metasulphobenzoate or a pharmacologically acceptable salt thereof to the intestine comprising a plurality of pellets having a composition of the invention.

The invention further provides, in a fourth aspect, a method of treating inflammatory bowel disease which comprises administering to a patient a dosage form of the invention.

Preferably, the rheological modifying super-disintegrant is croscarmellose but other rheological modifying super-disintegrants such as carmellose, crospovidone, sodium starch glycolate (ie sodium carboxymethyl starch), and other modified starches can be used. The suitability of, and optimal concentration of the super-disintegrant can be determined by simple experimentation. Usually, the super-disintegrant will be present in an amount of at least 10 percent, especially 10 to 30 percent, by weight of the composition.

The prednisolone metasulphobenzoate usually will be present in an amount of at least 5 percent, especially 5 to 20 percent, by weight of the composition.

It is presently preferred that the excipient matrix comprises a sugar, especially lactose, and a cellulose, especially microcrystalline cellulose. Suitably, the excipient matrix consists essentially of the rheological modifying agent, sugar and cellulose.

The composition of the invention usually will in the form of pellets having a diameter in the range 700–1700 μm, preferably 1000–1400 μm. These pellets suitably are prepared by dry mixing PRED-MSB with the components of the excipient matrix, adding water and mixing to form an extrudable paste. The paste is extruded through a tube or orifice, preferable a tube of at least 4 mm length and at least 1 mm diameter at a rate of 20 to 200 mm/min, spheronised on a rotating plate, and the resultant pellets dried in a fluidised bed.

The pellets can be uncoated but usually will be coated with an enteric coating. The coating material can be any suitable coating, eg. cellulose acetate phthalate, hydroxypropyl methyl cellulose phthalate, ethyl cellulose or polyvinyl acetate phthalate but the preferred coating material is an anionic polymer, especially one which is insoluble in gastric juice and in intestinal fluid below pH 7 but is soluble in lower intestinal fluid, optionally in admixture with a neutral insoluble but permeable polymer. The presently preferred anionic polymers are anionic carboxylic polymers, i.e. polymers in which the anionic groups are at least predominantly free carboxylic and/or esterified carboxylic groups. It is particularly preferred that the anion polymers should be acrylic polymers and the presently most preferred polymers are partly methyl esterified methacrylic acid polymers in which the ratio of free acid groups to ester groups is about 1:1 (available from Röhm Pharma GmbH, Darmstadt, Germany under the Registered Trade Mark "Eudragit L"), or especially, about 1:2 (available from Röhm Pharma GmbH, Darmstadt, Germany under the Registered Trade Mark "Eudragit S"). The neutral insoluble but permeable polymers preferably are acrylic ester polymers, especially methylmethacrylate ester copolymers with ethylacrylate. Suitably, the molecular ratio of anionic polymer to neutral polymer is in the range 5:1 to 1:5, especially 3:1 to 1:3, most preferably 1:1 to 1:3.

The coating can be applied to the pellets by any suitable known coating technique. In particular, conventional coating techniques such as spray or pan coating can be employed. Preferably, the coating is applied from aqueous dispersion.

The thickness of coating required on the pellets will depend upon the dissolution profile of the particular coating materials and possibly also upon the dissolution profile of any enteric coating on the dosage form, usually a capsule, containing the pellets. However, it is well within the ability of the man of average skill in the art to determine by trial-and-error experimentation the optimum thickness of a particular coating required for a particular dosage form of the invention. When using an aqueous dispersion of a partly methyl esterified methacrylic acid polymer of the Eudragit S type admixed with a methylmethacrylate/ethylacrylate copolymer, the amount of coating material usually will be between 15 and 30 (dry weight based on the uncoated granule) with 20 to 25 being preferred.

The coating can, and usually will, contain plasticiser and possibly other coating additives such as colouring agents, gloss producers, talc and/or magnesium stearate as well known in the coating art. In particular, anionic carboxylic acrylic polymers usually contain 10 to 25% by weight of a plasticiser especially diethyl phthalate, although the presence of such a plasticiser may not be necessary when using an aqueous suspension for coating.

Usually, the pellets will be contained in a capsule but they can be compressed into a tablet or otherwise formulated into an enteric dosage form. The capsule usually will be a soft or, preferably, hard gelatin capsule although other capsules which will dissolve in the small intestine can be used.

The capsule (or other dosage form) preferably is coated with an enteric coating which will protect it during passage through the stomach. Any conventional enteric coating material which is soluble in the small intestine can be used, eg. cellulose acetate phthalate, hydroxy propylmethyl cellulose phthalate or initially ethyl cellulose followed by polyvinyl acetate phthalate, but it is preferred to use an anionic polymer having an appropriate dissolution profile. The presently preferred polymers are anionic carboxylic polymers, i.e. polymers in which the anionic groups are at least predominantly free carboxylic and/or esterified carboxylic groups. It is particularly preferred that the polymers should be acrylic polymers and the presently most preferred polymers are partly methyl esterified methacrylic acid polymers in which the ratio of free acid groups to ester groups is about 1:1 (i.e. Eudragit L).

The capsule (or other dosage form) coating can, and usually will contain plasticiser and possibly other coating additives such as colouring agents, gloss producers, talc and/or magnesium stearate as well known in the coating art. In particular, anionic carboxylic acrylic polymers usually contain 10 to 25% by weight of a plasticiser especially diethyl phthalate.

Conventional coating techniques such as spray or pan coating are employed to apply the enteric coating to the capsule (or other dosage form).

The following Examples are provided to illustrate the dosage forms of the invention:

EXAMPLE I 5 wt % PRED-MSB was dry mixed with 40 wt % microcrystalline cellulose (Avicel™ PH 101), 50 wt % lactose and 5 wt % croscarmellose sodium (Ac-Di-Sol™). Water was added and the mixture mixed for 10 minutes to form an extrudable paste The paste was extruded from a 25 mm diameter bowl through a 1 mm diameter tube of about 5 mm length at a rate of about 100 mm/min and spheronised on an 8 in (20 cm) plate rotated at about 1000 rpm for 10 to 15 min to provide pellets having a diameter in the range 1000–1400 μm. The resultant pellets were dried at 50° C. for 30 min on a fluidised bed.

Figure 6:
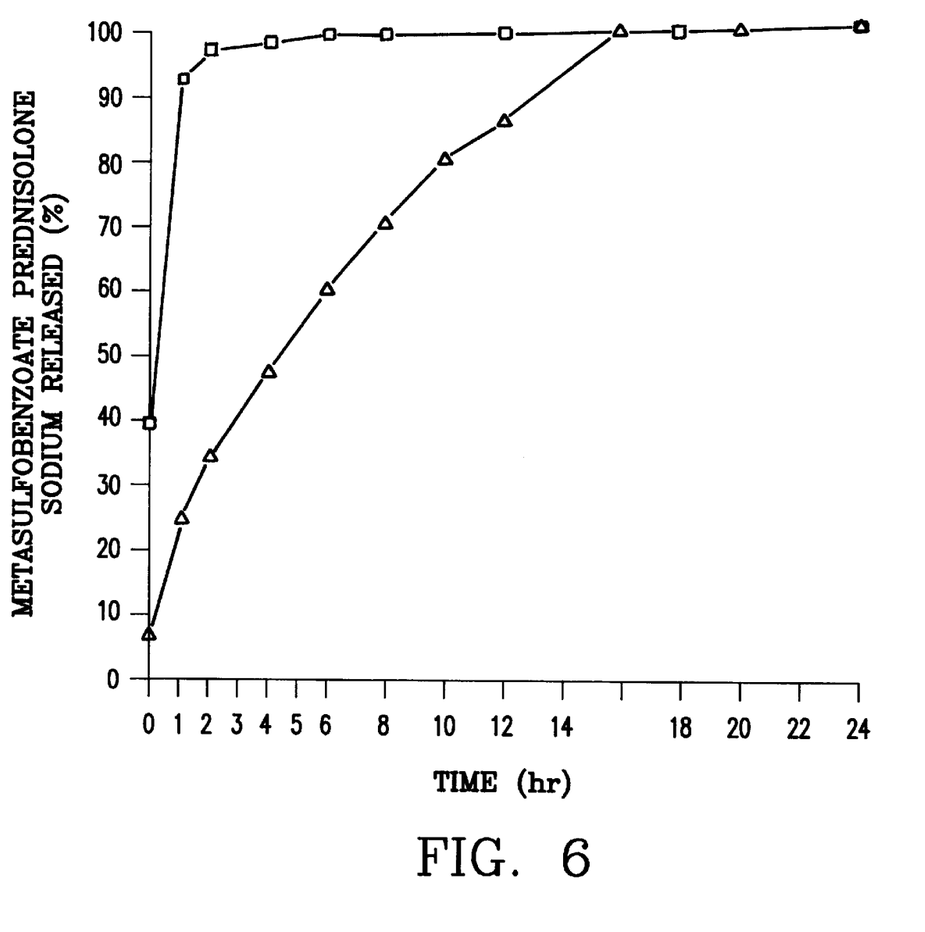
FIG. 6 shows the dissolution of 200 mg of pellets (700–1700 μm) containing 5 wt % PRED-MSB, 40 wt % microcrystalline cellulose (Avicel™ PH 101), 50 wt % lactose and 5 wt % croscarmellose sodium (Ac-Di-Sol™) at pH 1.2 (□) and pH 6.4 (Δ)

The rate of release of PRED-MSB from the pellets at pH 1.2 and pH 6.4 was measured and the results are shown in FIG. 6.

EXAMPLE II

Figure 7:
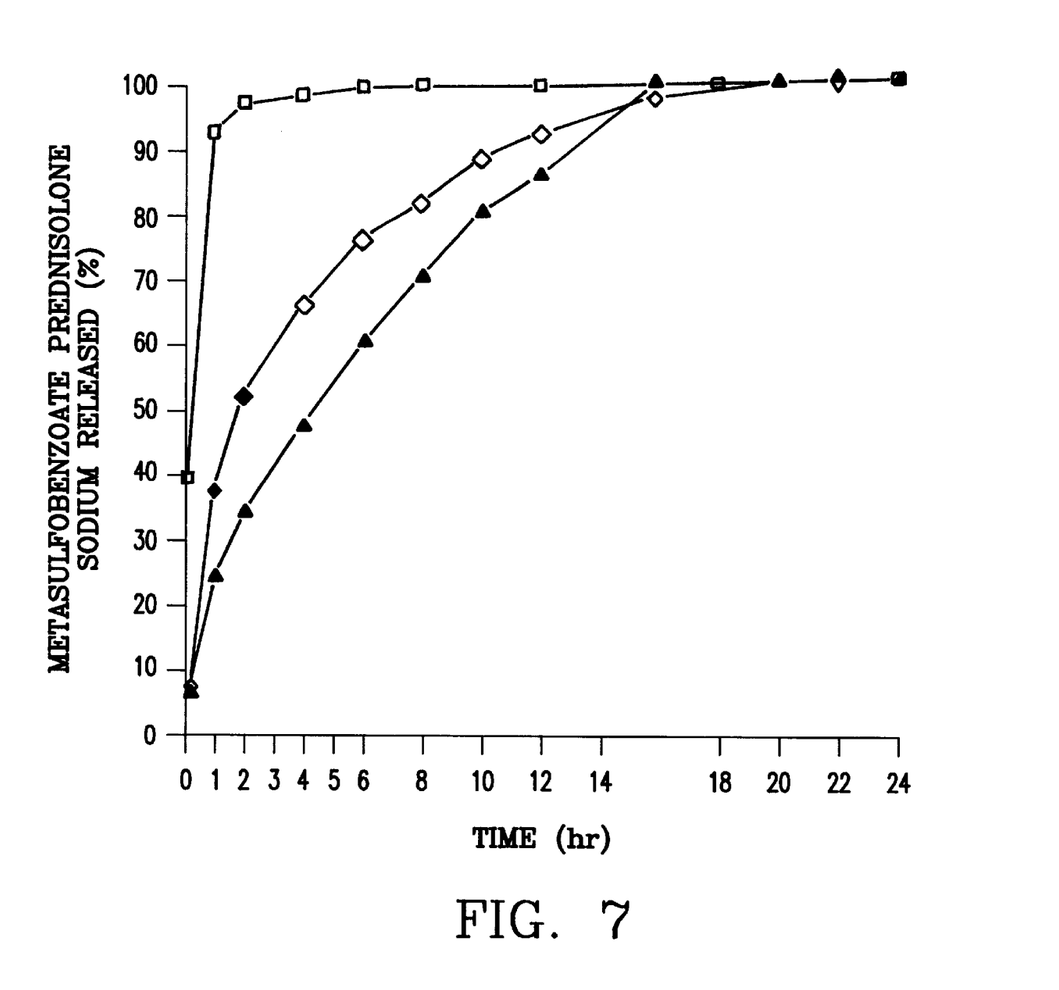
FIG. 7 shows the dissolution of 200 mg of pellets (700–1700 μm) containing 5 wt % PRED-MSB, 40 wt % microcrystalline cellulose (Avicel™ PH 101), 50 wt % lactose and 5 wt % croscarmellose sodium (Ac-Di-Sol™) at pH 1.2 (□) and pH 6.4 (▲) and 200 mg of pellets (700–1700

The procedure of Example I was repeated using a mixture of 5 wt % PRED-MSB, 40 wt % microcrystalline cellulose (Avicel™ PH 101), 50 wt % lactose and 5 wt % croscarmellose sodium (Ac-Di-Sol™). The rate of release of PRED-MSB from the pellets at pH 1.2 and pH 6.4 was measured and the results are shown in FIG. 7.

EXAMPLE III

The procedure of Example I was repeated using a mixture of 5 wt % PRED-MSB, 40 wt % microcrystalline cellulose (Avicel™ PH 101), 45 wt % lactose and 10 wt % croscarmellose sodium (Ac-Di-Sol™). The rate of release of PRED-MSB from the pellets at pH 6 .4 was measured and the results are shown in FIG. 7.

EXAMPLE IV

Figure 8:
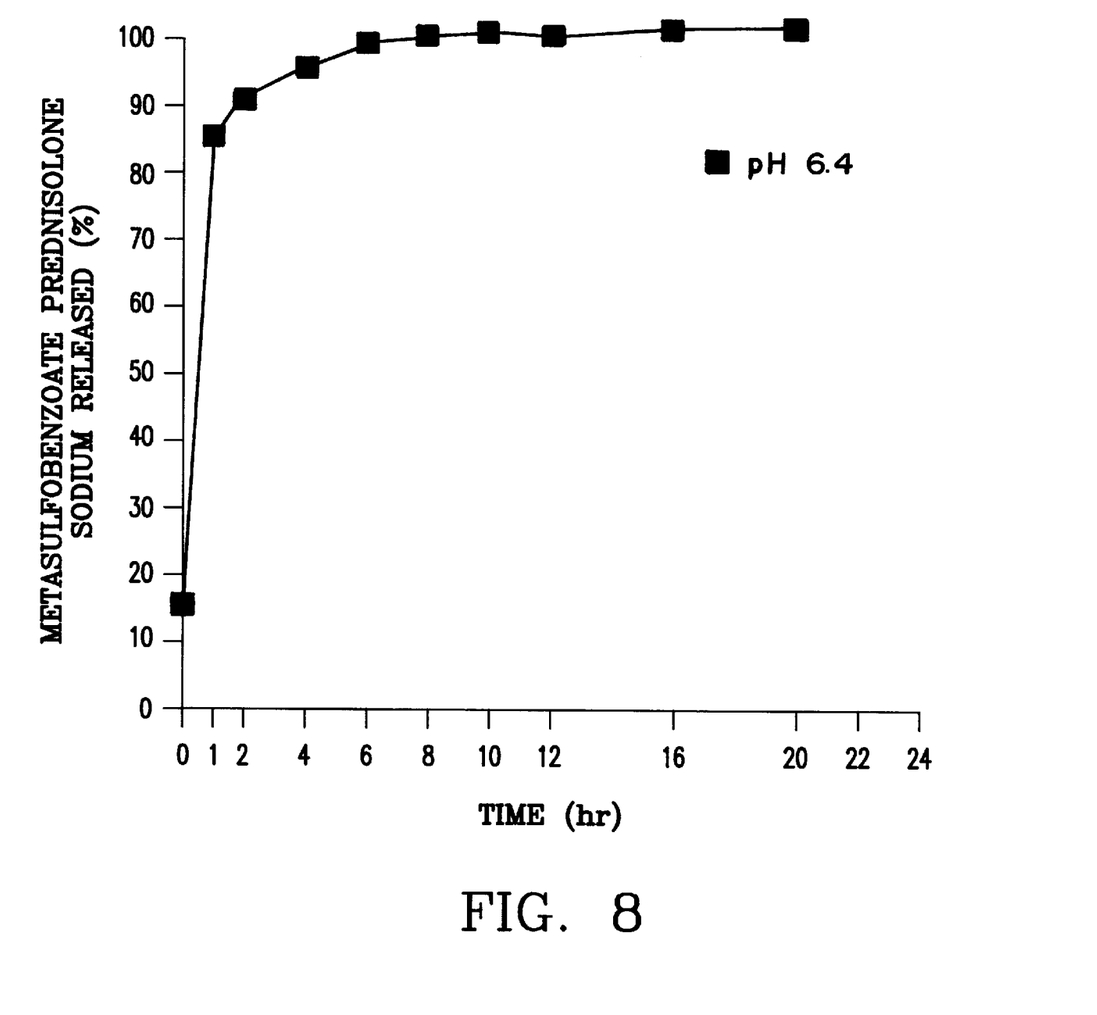
FIG. 8 shows the dissolution of 200 mg of pellets (700–1700 μm) containing 5 wt % PRED-MSB, 40 wt % microcrystalline cellulose (Avicel™ PH 101), 35 wt % lactose and 20 wt % croscarmellose sodium (Ac-Di-Sol™) at pH 6.4 (■)

The procedure of Example I was repeated using a mixture of 5 wt % PRED-MSB, 40 wt % microcrystalline cellulose (Avicel™ PH 101), 35wt % lactose and 20 wt % croscarmellose sodium (Ac-Di-Sol™). The rate of release of PRED-MSB from the pellets at pH 6.4 was measured and the results are shown in FIG. 8.

EXAMPLE V

The pellets of Example IV were coated with an Eudragit S100 coating to provide a theoretical weight gain on coating of 11.6% and filled (15.7 mg per capsule) into size 1 hard gelatin capsules. The filled capsules were coated with an Eudragit L100 coating to provide a theoretical weight gain on coating of 10.2%.

Figure 9:
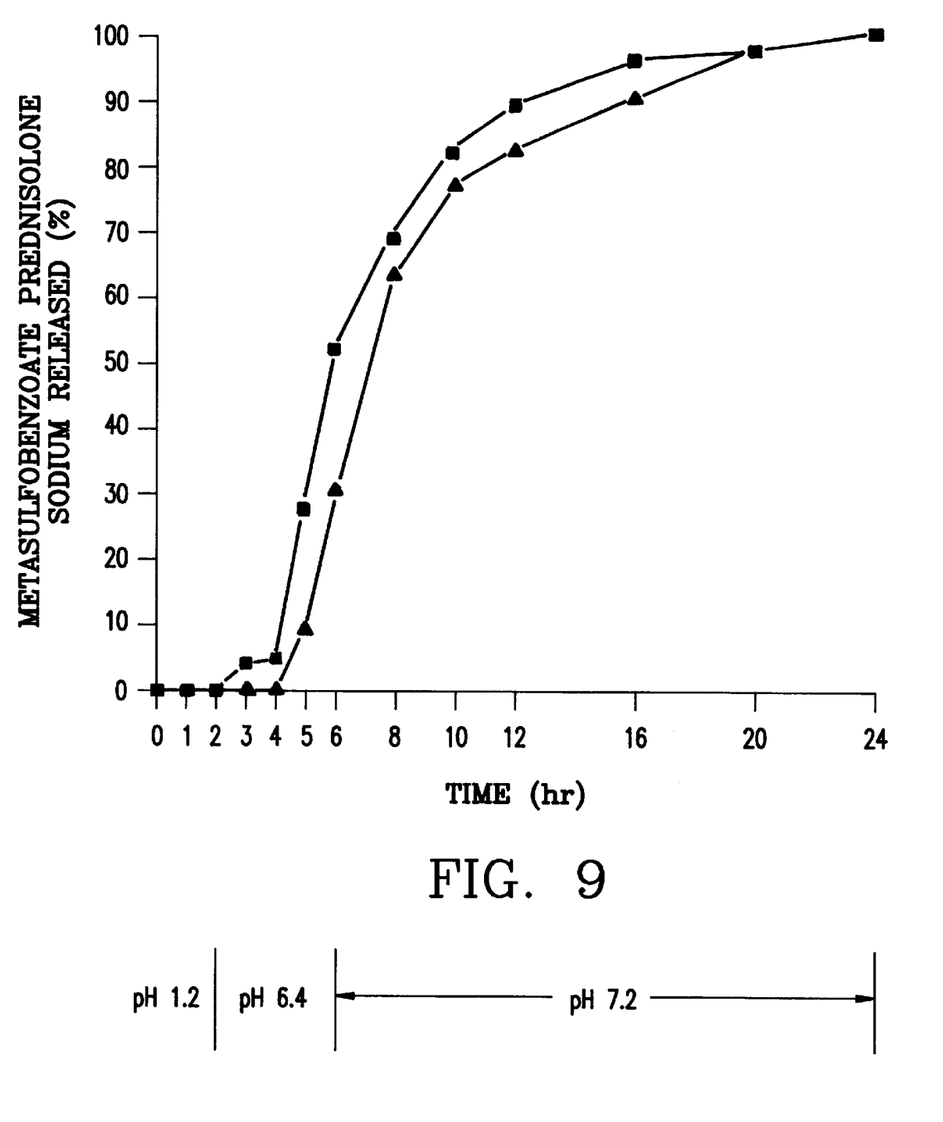
FIG. 9 shows the release profile of Eudragit L 100-coated size 1 capsules (theoretical weight gain on coating =11.6%) filled with Eudragit S 100-coated (■) or uncoated (▲) pellets (700–1700 μm) containing 5 wt % PRED-MSB, 40 wt % microcrystalline cellulose (Avicel™ PH 101), 35 wt % lactose and 20 wt % croscarmellose sodium (Ac-Di-Sol™) (theoretical weight gain on coating =10.2%) with 15.7 mg PRED-MSB per capsule (size 1).

The pH release profile of PRED-MSB from the coated capsules is shown in FIG. 9.

I claim:

1. A non-disintegratable solid enteric composition comprising prednisolone metasulphobenzoate or a pharmacologically acceptable salt thereof in an amount of 5 to 20 percent by weight of the composition in an excipient matrix characterized in that the rate of dissolution of the prednisolone metasulphobenzoate or a pharmacologically acceptable salt thereof at pH 6.5 is increased (compared with an otherwise identical composition) by the presence in the matrix of a rheological modifying super-disintegrant selected from carmellose, crospovidone, sodium starch glycolate (i.e., sodium carboxymethyl starch), and other modified starches in an amount of at least 5 percent by weight of the composition but insufficient to cause disintegration.

2. A composition as claimed in claim 1, wherein the rheological modifying super-disintegrant is croscarmellose.

3. A composition as claimed in claim 1, wherein the rheological modifying super-disintegrant is present in an amount of 10 to 30 percent by weight of the composition.

4. A composition as claimed in claim 1, wherein the excipient matrix comprises a sugar and a cellulose.

5. A composition as claimed in claim 4, wherein the excipient matrix consists essentially of the rheological modifying super-disintegrant, sugar and cellulose.

6. A composition as claimed in claim 5, wherein the sugar is lactose and the cellulose is microcrystalline cellulose.

7. A composition as claimed in claim 1 in the form of an uncoated pellet.

8. A composition as claimed in claim 1 in the form of a pellet coated with an enteric coating.

9. An enterically administrable pharmaceutical dosage form for selectively administering prednisolone metasulphobenzoate or a pharmacologically acceptable salt thereof to the intestine comprising a plurality of pellets as claimed in claim 8.

10. An enterically administrable pharmaceutical dosage form for selectively administering prednisolone metasulphobenzoate or a pharmacologically acceptable salt thereof to the intestine comprising a plurality of pellets as claimed in claim 7.

11. A method of treating inflammatory bowel disease which comprises administering to a patient having the disease a dosage form as claimed in claim 9.

12. A method of treating inflammatory bowel disease which comprises administering to a patient having the disease a dosage form as claimed in claim 10.

13. A non-disintegratable solid enteric composition comprising prednisolone metasulphobenzoate or a pharmacologically acceptable salt thereof in an amount 5 to 20 percent by weight of the composition and containing a rheological modifying super-disintegrant selected from carmellose, crospovidone, sodium starch glycolate (i.e., sodium carboxymethyl starch), and other modified starches in an amount to increase the rate of dissolution at pH 6.5 of the prednisolone metasulphobenzoate or a pharmacologically acceptable salt thereof from the composition compared to where the rheological modifying super-disintegrant is omitted but insufficient to cause disintegration of the composition.

14. A non-disintegratable solid enteric composition comprising prednisolone metasulphobenzoate or a pharmacologically acceptable salt thereof in an amount of 5 to 20 percent by weight of the composition in an excipient matrix characterized in that the rate of dissolution of the prednisolone metasulphobenzoate or a pharmacologically acceptable salt thereof at pH 6.5 is increased (compared with an otherwise identical composition) by the presence in the matrix of a rheological modifying super-disintegrant in an amount of at least 5 percent by weight of the composition but insufficient to cause disintegration, said excipient matrix consisting essentially of the rheological modifying super-disintegrant, lactose and microcrystalline cellulose.

* * * * *